(12) United States Patent
Khangura

(10) Patent No.: US 9,636,197 B2
(45) Date of Patent: May 2, 2017

(54) APPARATUS FOR USER HAVING TEETH

(71) Applicant: Gurmeet Khangura, Mission (CA)

(72) Inventor: Gurmeet Khangura, Mission (CA)

( * ) Notice: Subject to any disclaimer, the term of this patent is extended or adjusted under 35 U.S.C. 154(b) by 159 days.

(21) Appl. No.: 14/534,403

(22) Filed: Nov. 6, 2014

(65) Prior Publication Data

US 2016/0128816 A1 May 12, 2016

(51) Int. Cl.
*A61C 19/00* (2006.01)
*A61C 19/06* (2006.01)
*A46B 9/04* (2006.01)

(52) U.S. Cl.
CPC ............ *A61C 19/066* (2013.01); *A46B 9/045* (2013.01); *A61C 19/063* (2013.01)

(58) Field of Classification Search
CPC ................................ A61C 19/66; A46B 9/045
USPC ............................................................ 433/29
See application file for complete search history.

(56) References Cited

U.S. PATENT DOCUMENTS

| 3,769,652 | A | | 11/1973 | Rainer | |
|---|---|---|---|---|---|
| 4,224,710 | A | | 9/1980 | Solow | |
| 5,175,901 | A | * | 1/1993 | Rabinowitz | ............ A46B 9/045 15/167.1 |
| 6,223,376 | B1 | * | 5/2001 | Lee | ........................ A46B 9/026 15/22.1 |
| 6,353,956 | B1 | | 3/2002 | Berge | |
| 8,745,802 | B2 | | 6/2014 | Steur | |
| 2003/0176891 | A1 | | 9/2003 | Frederic | |
| 2003/0178885 | A1 | * | 9/2003 | Weihrauch | ............ A46B 9/045 300/21 |
| 2011/0072605 | A1 | | 3/2011 | Steur | |
| 2011/0154595 | A1 | | 6/2011 | Hill | |
| 2012/0183919 | A1 | * | 7/2012 | Levine | ................ A61C 19/063 433/29 |
| 2012/0318289 | A1 | | 12/2012 | Sahoo | |
| 2013/0014331 | A1 | | 1/2013 | Garner et al. | |
| 2013/0067665 | A1 | | 3/2013 | Sowinski | |
| 2013/0333126 | A1 | | 12/2013 | Miller | |
| 2014/0093836 | A1 | | 4/2014 | Wolpo | |

FOREIGN PATENT DOCUMENTS

| CA | 2609556 | 11/2006 |
|---|---|---|
| CA | 2738902 | 4/2010 |
| CA | 2748419 | 7/2010 |
| CA | 2785085 | 6/2011 |
| WO | 2013098718 | 7/2013 |

* cited by examiner

*Primary Examiner* — Paula J Stice
(74) *Attorney, Agent, or Firm* — Giuseppe Mariconda

(57) ABSTRACT

Apparatus is for user having teeth. Apparatus includes upper oral delivery mouthpiece and lower oral delivery mouthpiece each configured to be positioned in the mouth of the user. Upper oral delivery mouthpiece includes upper bendable assembly configured to urge upper oral delivery mouthpiece to conform, at least in part, to a curvature of the upper teeth of the user. Lower oral delivery mouthpiece includes lower bendable assembly configured to urge lower oral delivery mouthpiece to conform, at least in part, to a curvature of the lower teeth of the user.

19 Claims, 12 Drawing Sheets

APPARATUS FOR USER HAVING TEETH

TECHNICAL FIELD

Some aspects generally relate to (and are not limited to) an apparatus for a user having a mouth leading to an oral cavity in which upper teeth having upper opposite sides are positioned, and in which lower teeth having lower opposite sides are positioned.

SUMMARY

It will be appreciated there exists a need to mitigate (at least in part) at least one problem associated with oral appliances. After much study of the known systems and methods with experimentation, an understanding of the problem and its solution has been identified and is articulated as follows:

A mouthguard is a protective device for the mouth that covers the teeth and gums to prevent and reduce injury to the teeth, arches, lips and gums. A mouthguard is most often used to prevent injury in contact sports, as a treatment for bruxism, or as part of certain dental procedures, such as tooth bleaching. Depending on application, it may also be called a mouth protector, a mouth piece, a gumshield, a gumguard, a nightguard, an occlusal splint, a bite splint, or a bite plane.

A toothbrush is an oral hygiene instrument used to clean the teeth and gums that consists of a head of tightly clustered bristles mounted on a handle, which facilitates the cleansing of hard-to-reach areas of the mouth. Toothpaste, which often contains fluoride, is commonly used in conjunction with a toothbrush to increase the effectiveness of tooth brushing. It was discovered that existing technology related to existing toothbrushes may be further improved, to better clean the teeth of a user.

To mitigate, at least in part, at least one problem associated with existing oral appliances, there is provided (in accordance with a major aspect) an apparatus. The apparatus is for a user having a mouth leading to an oral cavity in which upper teeth having upper opposite sides are positioned, and in which lower teeth having lower opposite sides are positioned. The apparatus includes an upper intraoral plastic u-shaped mouthpiece configured to cradle, at least in part, the upper teeth of the user once the upper intraoral plastic u-shaped mouthpiece is operatively received in the mouth of the user just so. The apparatus also includes an upper tooth-bristle assembly configured to operatively affix to the upper intraoral plastic u-shaped mouthpiece in such a way that the upper tooth-bristle assembly faces the upper opposite sides of the upper teeth of the user once the upper intraoral plastic u-shaped mouthpiece is operatively received in the mouth of the user just so. The apparatus also includes a lower intraoral plastic u-shaped mouthpiece configured to cradle, at least in part, the lower teeth of the user once the lower intraoral plastic u-shaped mouthpiece is operatively received in the mouth of the user just so. The apparatus also includes a lower tooth-bristle assembly configured to operatively affix to the lower intraoral plastic u-shaped mouthpiece in such a way that the lower tooth-bristle assembly faces the lower opposite sides of the lower teeth of the user once the lower intraoral plastic u-shaped mouthpiece is operatively received in the mouth of the user just so.

To mitigate, at least in part, at least one problem associated with existing oral appliances, there is provided (in accordance with a major aspect) a method. A method is for a user having a mouth leading to an oral cavity in which upper teeth having upper opposite sides are positioned, and in which lower teeth having lower opposite sides are positioned. The method includes (and is not limited to) operatively affixing an upper tooth-bristle assembly to an upper intraoral plastic u-shaped mouthpiece. This is done in such a way that the upper tooth-bristle assembly faces the upper opposite sides of the upper teeth of the user once the upper intraoral plastic u-shaped mouthpiece is operatively received in the mouth of the user, and the upper intraoral plastic u-shaped mouthpiece cradles, at least in part, the upper teeth of the user. The method also includes operatively affixing a lower tooth-bristle assembly to a lower intraoral plastic u-shaped mouthpiece. This is done in such a way that the lower tooth-bristle assembly faces the lower opposite sides of the lower teeth of the user once the lower intraoral plastic u-shaped mouthpiece is operatively received in the mouth of the user, and the lower intraoral plastic u-shaped mouthpiece cradles, at least in part, the lower teeth of the user.

To mitigate, at least in part, at least one problem associated with existing oral appliances, there is provided (in accordance with a major aspect) an apparatus. The apparatus is for a user having a mouth leading to an oral cavity in which upper teeth having upper opposite sides are positioned, and in which lower teeth having lower opposite sides are positioned. The apparatus includes an upper oral delivery mouthpiece being configured to be positioned in the mouth of the user in such a way that the upper oral delivery mouthpiece provides, at least in part, oral treatment to the upper teeth of the user once the upper oral delivery mouthpiece is operatively received in the mouth of the user just so. The apparatus also includes a lower oral delivery mouthpiece configured to be positioned in the mouth of the user in such a way that the lower oral delivery mouthpiece provides, at least in part, oral treatment to the lower teeth of the user once the lower oral delivery mouthpiece is operatively received in the mouth of the user just so.

To mitigate, at least in part, at least one problem associated with existing oral appliances, there is provided (in accordance with a major aspect) an apparatus for user. The apparatus includes an upper oral delivery mouthpiece and a lower oral delivery mouthpiece each configured to be positioned in the mouth of the user. Upper oral delivery mouthpiece includes an upper bendable assembly configured to urge upper oral delivery mouthpiece to conform, at least in part, to a curvature of the upper teeth of the user. The lower oral delivery mouthpiece includes lower bendable assembly configured to urge lower oral delivery mouthpiece to conform, at least in part, to a curvature of the lower teeth of the user.

Other aspects are identified in the claims.

Other aspects and features of the non-limiting embodiments may now become apparent to those skilled in the art upon review of the following detailed description of the non-limiting embodiments with the accompanying drawings.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
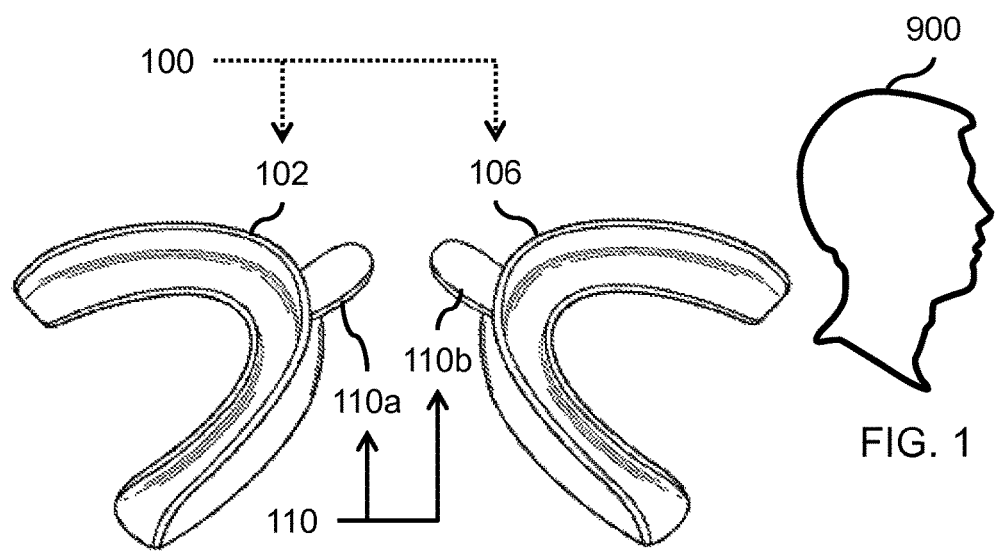
FIG. 1 depicts a view of an embodiment of an apparatus for a user having a mouth leading to an oral cavity in which upper teeth having upper opposite sides are positioned, and in which lower teeth having lower opposite sides are positioned.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted.

Corresponding reference characters indicate corresponding components throughout the several figures of the Drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, but well-understood, elements that are useful or necessary in commercially feasible embodiments are often not depicted to provide a less obstructed view of the embodiments of the present disclosure.

LISTING OF REFERENCE NUMERALS USED
IN THE DRAWINGS 100 apparatus
102 upper oral delivery mouthpiece
104 upper tooth-bristle assembly
104a first upper tooth-bristle assembly
104b second upper tooth-bristle assembly
104c upper base section
104d upper bristle field
104e upper base section
104f upper bristle field
106 lower oral delivery mouthpiece
108 lower tooth-bristle assembly
108a first lower tooth-bristle assembly
108b second lower tooth-bristle assembly
108c lower base section
108d lower bristle field
108e lower base section
108f lower bristle field
110 handle assembly
110a first handle assembly
110b second handle assembly
112a upper bendable assembly
112b lower bendable assembly
114a first movable flap assembly
114b second movable flap assembly
116a upper optical fiber
116b lower optical fiber
118a first wire
118b second wire
120 light-treatment assembly
122a inner wall assembly
122b outer wall assembly
124a inner wall assembly
124b outer wall assembly
126 ortho bracket
128a upper attachment assembly
128b lower attachment assembly
900 user
901 mouth
902 upper teeth
904 sides
906 lower teeth
908 sides
910 direction arrows
912 directional arrow
914 gum line
916 tooth
918 gum

DETAILED DESCRIPTION OF THE
NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the invention is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments, and any equivalent thereof) are described regarding the drawings. It should be understood that the invention is limited to the subject matter provided by the claims, and that the invention is not limited to the particular aspects depicted and described.

FIG. 1 depicts a view of an embodiment of an apparatus 100 for a user 900 (also depicted in FIG. 3) having a mouth 901 leading to an oral cavity in which upper teeth 902 having upper opposite sides 904 (also depicted in FIG. 4A) are positioned, and in which the lower teeth 906 having lower opposite sides 908 (also depicted in FIG. 4A) are positioned. FIG. 1 depicts a perspective view of the apparatus 100.

In accordance with a major embodiment, the apparatus 100 includes an upper oral delivery mouthpiece 102 and a lower oral delivery mouthpiece 106. The upper oral delivery mouthpiece 102 is configured to be positioned in the mouth 901 of the user 900 in such a way that the upper oral delivery mouthpiece 102 provides, at least in part, oral treatment to the upper teeth 902 of the user 900 once the upper oral delivery mouthpiece 102 is operatively received in the mouth 901 of the user 900 just so. The lower oral delivery mouthpiece 106 is configured to be positioned in the mouth 901 of the user 900 in such a way that the lower oral delivery mouthpiece 106 provides, at least in part, oral treatment to the lower teeth 906 of the user 900 once the lower oral delivery mouthpiece 106 is operatively received in the mouth 901 of the user 900 just so. A technical effect of this embodiment is that the upper oral delivery mouthpiece 102 and the lower oral delivery mouthpiece 106 provide oral treatment independently of each other to the upper teeth 902 and the lower teeth 906, respectively. In addition, another technical effect for this embodiment is that oral treatment to be provided by the upper oral delivery mouthpiece 102 may include (and is not limited to) prevention of oral disease, cavities, gum disease, mouth cancer, bad breath, staining of teeth, and/or cosmically enhancement of teeth. For instance, the upper oral delivery mouthpiece 102 and the lower oral delivery mouthpiece 106 are movable relative to each other in such a way that the upper teeth 902 and the lower teeth 906 of the user 900 receive oral treatment independently of each other.

In accordance with an option, the upper oral delivery mouthpiece 102 and the lower oral delivery mouthpiece 106 are configured to be manually operatively movable within the mouth 901 of the user 900 without assistance from an electric power source.

In accordance with a major embodiment, the apparatus 100 includes an upper oral delivery mouthpiece 102 (also called an upper intraoral plastic u-shaped mouthpiece) and a lower oral delivery mouthpiece 106 (also called a lower intraoral plastic u-shaped mouthpiece). The upper oral delivery mouthpiece 102 is configured to cradle, at least in part, the upper teeth 902 of the user 900 (depicted in FIG. 3) once the upper oral delivery mouthpiece 102 is operatively received in the mouth 901 of the user 900 just so. The lower oral delivery mouthpiece 106 is configured to cradle, at least in part, the lower teeth 906 of the user 900 (depicted in FIG. 3) once the lower oral delivery mouthpiece 106 is operatively received in the mouth 901 of the user 900 just so.

It will be appreciated that there is provided a method. The method is for a user having a mouth leading to an oral cavity in which upper teeth having upper opposite sides are positioned, and in which lower teeth having lower opposite sides are positioned. The method includes (and is not limited to) operatively affixing an upper tooth-bristle assembly 104 to an upper oral delivery mouthpiece 102. This is done in such a way that the upper tooth-bristle assembly 104 faces the upper opposite sides of the upper teeth of the user once the upper oral delivery mouthpiece 102 is operatively received in the mouth of the user, and the upper oral delivery mouthpiece 102 cradles, at least in part, the upper teeth of the user. The method also includes operatively affixing a lower tooth-bristle assembly 108 to a lower oral delivery mouthpiece 106. This is done in such a way that the lower tooth-bristle assembly 108 faces the lower opposite sides of the lower teeth of the user once the lower oral delivery mouthpiece 106 is operatively received in the mouth of the user, and the lower oral delivery mouthpiece 106 cradles, at least in part, the lower teeth of the user.

In accordance with an option, the apparatus 100 further includes (in general terms) a handle assembly 110. The handle assembly 110 is configured to operatively attach to the upper oral delivery mouthpiece 102. The handle assembly 110 is also configured to attach to the lower oral delivery mouthpiece 106. This is done in such a way that the handle assembly 110 is usable for inserting and positioning the upper oral delivery mouthpiece 102 and the lower oral delivery mouthpiece 106 into the mouth 901 of the user 900.

In accordance with the embodiment depicted in FIG. 1, the handle assembly 110 includes a first handle assembly 110a and a second handle assembly 110b. The first handle assembly 110a is configured to operatively attach to the upper oral delivery mouthpiece 102. The second handle assembly 110b is configured to operatively attach to the lower oral delivery mouthpiece 106. The first handle assembly 110a and the second handle assembly 110b are disconnected (disjoined) from each other. It will be appreciated that the first handle assembly 110a and the second handle assembly 110b may be joined or attached together (if so desired).

In accordance with a specific option, the upper oral delivery mouthpiece 102 and the lower oral delivery mouthpiece 106 each include a flexible silicone material (and any equivalent thereof). In accordance with another specific option, the upper oral delivery mouthpiece 102 and the lower oral delivery mouthpiece 106 each include a flexible plastic material (and any equivalent thereof).

Figure 2A:
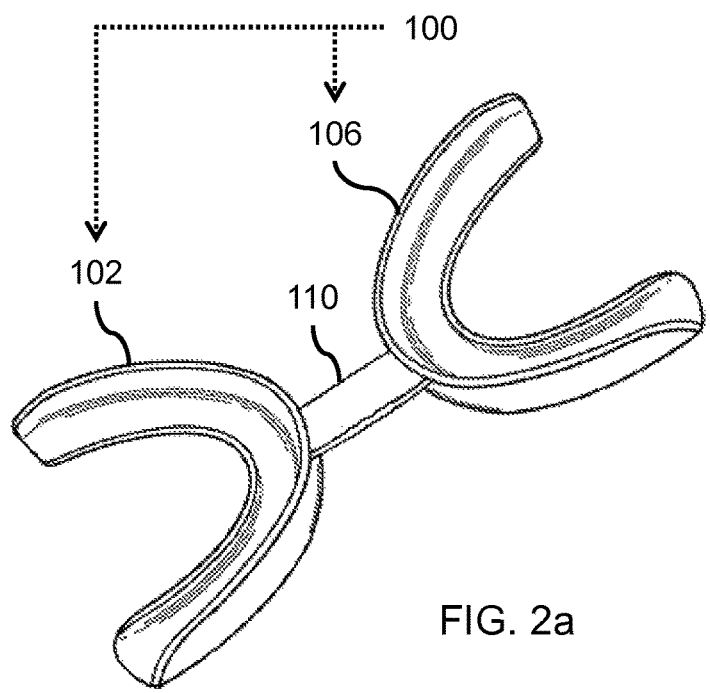
FIGS. 2A, 2B, 2C, 2D, 2E and 2F depict views of embodiments of the apparatus of FIG. 1.
Figure 2B:
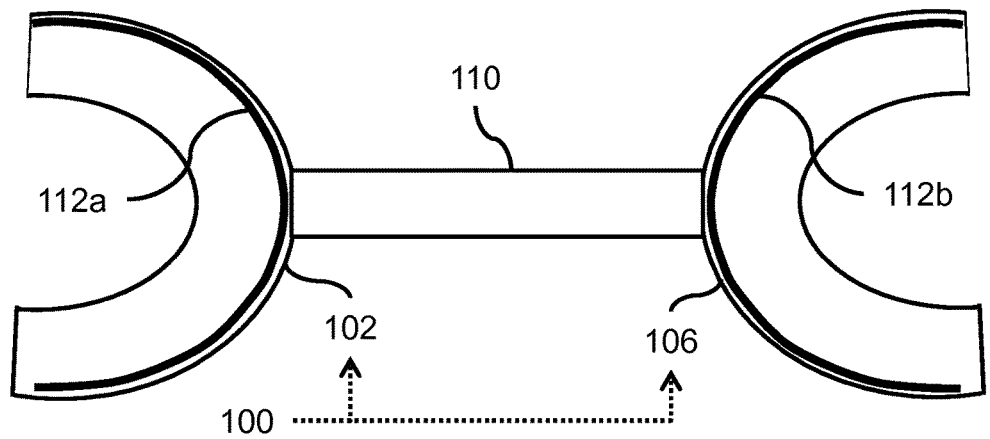
Figure 2C:
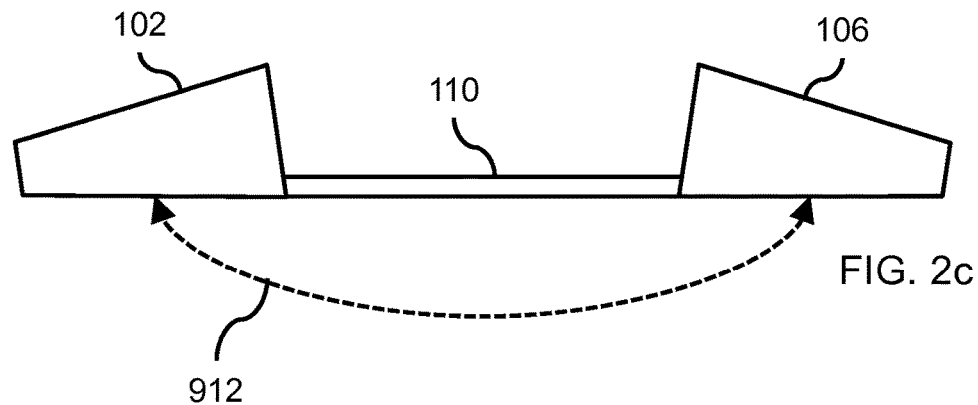
Figure 2D:
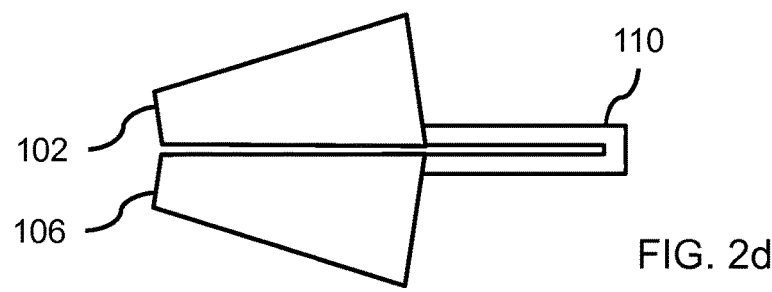
Figure 2E:
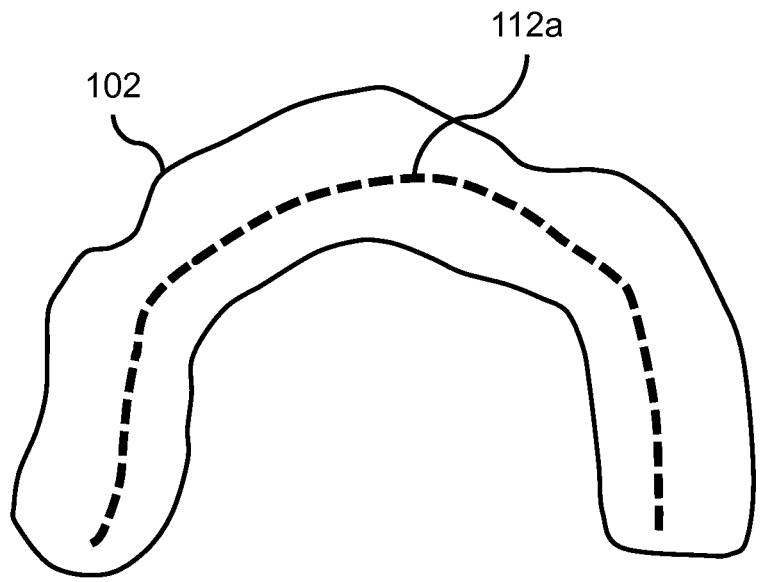
Figure 2F:
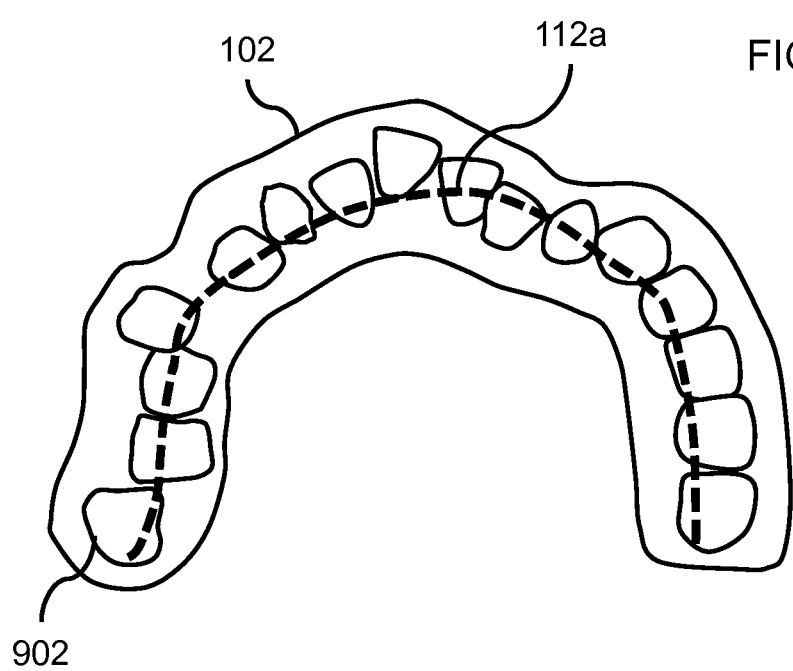

FIGS. 2A, 2B, 2C, 2D, 2E and 2F depict views of embodiments of the apparatus 100 for the user 900 (depicted in FIG. 3) having a mouth 901 leading to an oral cavity in which upper teeth 902 having upper opposite sides 904 (depicted in FIG. 4A) are positioned, and in which lower teeth 906 having lower opposite sides 908 (depicted in FIG. 4A) are positioned. FIG. 2A depicts a perspective view. FIGS. 2b, 2e and 2f depict top views. FIG. 2c and FIG. 2d depict side views.

Referring to the embodiment depicted in FIG. 2A, the handle assembly 110 is configured to attach the upper oral delivery mouthpiece 102 to the lower oral delivery mouthpiece 106 in such a way that the handle assembly 110 extends between the upper oral delivery mouthpiece 102 and the lower oral delivery mouthpiece 106. Specifically, the handle assembly 110 is attached to the top arched curve of the upper oral delivery mouthpiece 102 and the lower oral delivery mouthpiece 106.

Referring to the embodiment depicted in FIG. 2b, the apparatus 100 further includes an upper bendable assembly 112a. The upper bendable assembly 112a includes a malleable material. The upper bendable assembly 112a is positioned (embedded in) along the interior of the upper oral delivery mouthpiece 102. The upper bendable assembly 112a is configured to bend in response to receiving a predetermined amount of a bending force. This is done in such a way that the upper oral delivery mouthpiece 102 bends and conforms, at least in part, to a curvature of the upper teeth 902 of the user 900. This improves (at least in part) the adapting of the upper oral delivery mouthpiece 102 to the upper teeth 902 of the user 900 (depicted in FIG. 3) for the case where the user 900 has crowded teeth or misshaped teeth, etc. The upper bendable assembly 112a is also configured to not bend in response to not receiving the predetermined amount of the bending force in such a way that the upper oral delivery mouthpiece 102 remains, at least in part, in conforming shape to the curvature of the upper teeth 902 of the user 900.

In accordance with an embodiment, the upper oral delivery mouthpiece 102 includes an upper bendable assembly 112a embedded in the upper oral delivery mouthpiece 102, and the upper bendable assembly 112a configured to urge the upper oral delivery mouthpiece 102 to conform, at least in part, to a curvature of the upper teeth 902 of the user 900. The lower oral delivery mouthpiece 106 includes a lower bendable assembly 112b embedded in the lower oral delivery mouthpiece 106, and the lower bendable assembly 112b configured to urge the lower oral delivery mouthpiece 106 to conform, at least in part, to a curvature of the lower teeth 906 of the user 900. A technical effect for this embodiment is improved adapting to the upper teeth 902 of the user 900 such as, to crowded teeth or misshaped teeth. Another technical effect for this embodiment is improved adapting to the lower teeth 906 of the user 900 such as, to crowded teeth or misshaped teeth. This permits or allows the user to mold to the dentitions, crowding, and/or misaligned teeth. The lower bendable assembly 112b and the lower bendable assembly 112b may include a mental mesh or a wire (at least one or more wires).

The upper bendable assembly 112a is configured to bend the upper oral delivery mouthpiece 102 and to place the upper oral delivery mouthpiece 102 in a relatively stable form or condition; this is in such a way that the upper oral delivery mouthpiece 102 is formed (shaped) to conform with the dental arch of the upper teeth 902 of the user 900 (whether the dental arch is relatively wider or narrower for different users). Similarly, the lower bendable assembly 112b is configured to bend the lower oral delivery mouthpiece 106 and to place the lower oral delivery mouthpiece 106 in a relatively stable form or condition; this is done in such a way that the lower oral delivery mouthpiece 106 is formed to conform with the dental arch of the lower teeth 906 of the user 900 (whether the dental arch is relatively wider or narrower for different users). It is appreciated that persons of skill in the art would understand that the upper bendable assembly 112a and the lower bendable assembly 112b are configured to permit custom fitting of the upper oral delivery mouthpiece 102 and the lower oral delivery mouthpiece 106 for the unique curves of the dental arches of a specific user, and that the upper oral delivery mouthpiece 102 and the lower oral delivery mouthpiece 106 remain so formed in a custom fit once positioned to do just so. The upper bendable assembly 112a and the lower bendable assembly 112b may include any type of material suitable for such purposes (such as, a wire or metal mesh, etc.).

The apparatus 100 further includes a lower bendable assembly 112b. The lower bendable assembly 112b includes a malleable material. The lower bendable assembly 112b is positioned along the interior of the lower oral delivery mouthpiece 106. The lower bendable assembly 112b is configured to bend in response to receiving a predetermined amount of a bending force. This is done in such a way that the lower oral delivery mouthpiece 106 bends and conforms, at least in part, to the curvature of the lower teeth 906 of the user 900. This arrangement improves (at least in part) adapting to the lower teeth 906 of the user 900 (such as, to crowded teeth or misshaped teeth, etc.). The lower bendable assembly 112b is also configured to not bend in response to not receiving the predetermined amount of the bending force. This is done in such a way that the lower oral delivery mouthpiece 106 remains, at least in part, in conforming shape to the curvature of the lower teeth 906 of the user 900. The directional arrow 912 depicts the path for folding the handle assembly 110.

By way of example, the upper bendable assembly 112a and the lower bendable assembly 112b may include, for example, a resilient flexible wire, a resilient bendable wire, a resilient mesh positioned or located inside the body of the upper oral delivery mouthpiece 102 and the body of the lower oral delivery mouthpiece 106. This arrangement allows the user 900 to place the apparatus 100 into the mouth 901 (depicted in FIG. 3), to bend the upper oral delivery mouthpiece 102 and the upper tooth-bristle assembly 104 in order to conform to the curvature of the teeth of the user 900 (thus better adapting the apparatus 100 to users having crowded teeth or misshaped teeth, etc.). The upper bendable assembly 112a and the lower bendable assembly 112b mitigate, at least in part, problems associated with cleaning crowded teeth, etc.

Referring to the embodiments depicted in FIG. 2c and FIG. 2d, the handle assembly 110 is configured to be resiliently bent to form a u-shape in response to receiving an application of a bending force. In addition, the handle assembly 110 is also configured to relax (become resiliently elongated) in response to removal of the bending force from the handle assembly 110. Generally, the handle assembly 110 is configured to be flexible but have some amount of stiffness.

Referring to the embodiments depicted FIGS. 2e and 2f, the upper oral delivery mouthpiece 102 is depicted. It will be appreciated that the same arrangement may be used or deployed in the lower oral delivery mouthpiece 106 of FIG. 1 (and the lower bendable assembly 112b as depicted in FIG. 2b) for use with the lower teeth 906 depicted in FIG. 3). As depicted, the user 900 of FIG. 1 has the upper teeth 902 that are classified as crowded teeth. The upper bendable assembly 112a of FIG. 2e is manipulated (changed) in such a way that the upper oral delivery mouthpiece 102 better fits (at least in part) the upper teeth 902 that are classified as crowded teeth (or classified as having mis-shaped dental arches. Once the upper bendable assembly 112a is manipulated just so, the upper oral delivery mouthpiece 102 is inserted into the mouth of the user 900 (as depicted in FIG. 20. As depicted in FIG. 2f, the upper oral delivery mouthpiece 102 has a shape that conforms, at least in part, the outer surfaces of the upper teeth 902 of the user 900. The technical effect for this arrangement is improved interaction between the upper teeth 902 and the upper oral delivery mouthpiece 102.

Figure 3:
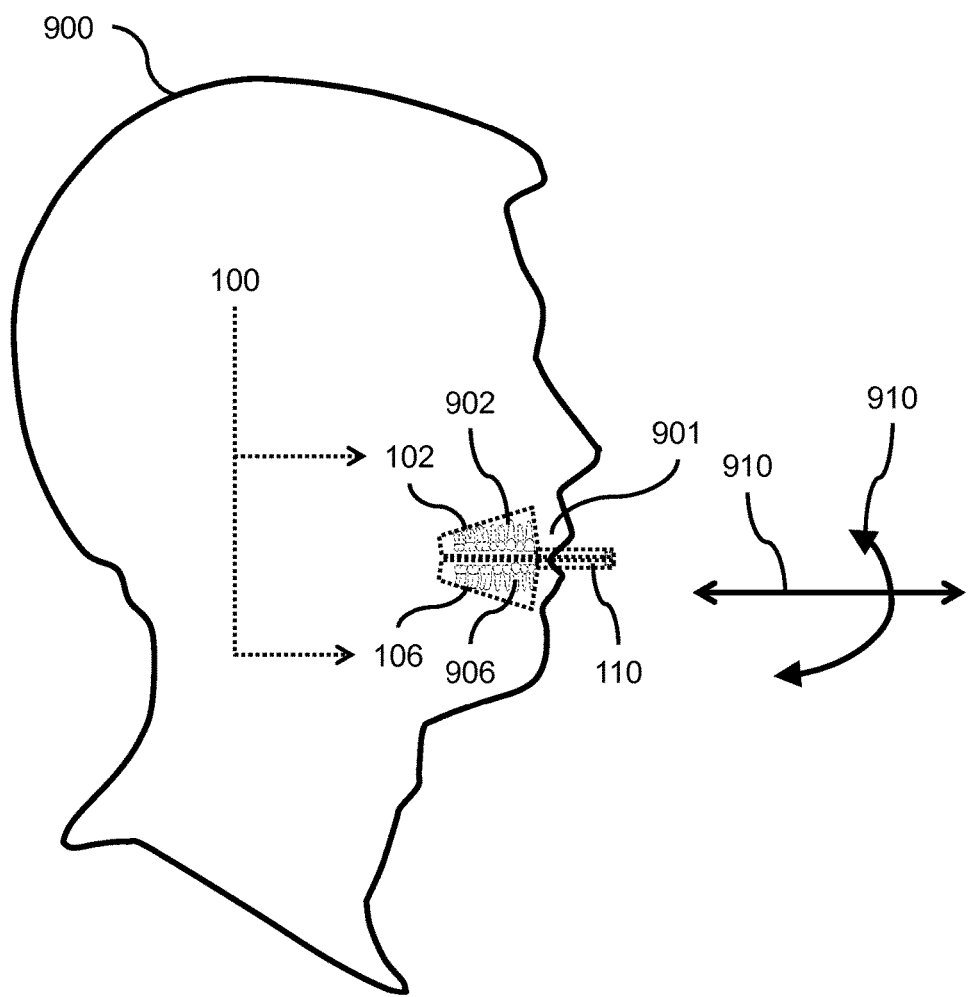
FIG. 3 depicts a view of an embodiment of the apparatus of FIG. 1.

FIG. 3 depicts a cross-sectional view through the apparatus 100 for the user 900 (depicted in FIG. 3) having a mouth 901 leading to an oral cavity in which upper teeth 902 having upper opposite sides 904 (depicted in FIG. 4A) are positioned, and in which lower teeth 906 having lower opposite sides 908 (depicted in FIG. 4A) are positioned. FIG. 3 depicts a cross sectional view.

As depicted in FIG. 3, the handle assembly 110 extends (when in use) outside of the mouth 901 of the user 900 once the upper oral delivery mouthpiece 102 and the lower oral delivery mouthpiece 106 are operatively received in the mouth 901 of the user 900.

Referring to the embodiment depicted in FIG. 3, the handle assembly 110 is configured to allow (facilitate) relative movement between the upper oral delivery mouthpiece 102 and the lower oral delivery mouthpiece 106. This arrangement allows the upper oral delivery mouthpiece 102 and the lower oral delivery mouthpiece 106 to accommodate different over bites for different users. The handle assembly 110 mitigates, at least in part, problems associated with cleaning crowded teeth. The handle assembly 110 includes a u-shaped member connecting the upper oral delivery mouthpiece 102 with the lower oral delivery mouthpiece 106. The handle assembly 110 extends from the mouth 901 of the user 900 (when used as depicted) so that the user may manipulate placement of the apparatus 100 as required to clean the teeth of the user 900. The handle assembly 110 may be configured to fold, at least in part, on itself (as depicted).

Referring to the embodiment depicted in FIG. 3, the apparatus 100 is flexible allowing for improved coverage to aligned and misaligned teeth. The apparatus 100 functions by placing the upper oral delivery mouthpiece 102 and the upper tooth-bristle assembly 104 into the mouth 901 of the user 900. The user 900 bites down (slightly) on the upper oral delivery mouthpiece 102 and the upper tooth-bristle assembly 104, and moves the handle assembly 110 left and right, up and down (in a wiggling motion) as indicated in direction arrows 910. For instance, the user 900 may use the modified Stillman brushing technique when cleaning the teeth with the apparatus 100.

In accordance with an option, the upper tooth-bristle assembly 104 and the lower tooth-bristle assembly 108 are configured to be manually operatively movable within the mouth 901 of the user 900 without assistance from an electric power source.

Figure 4A:
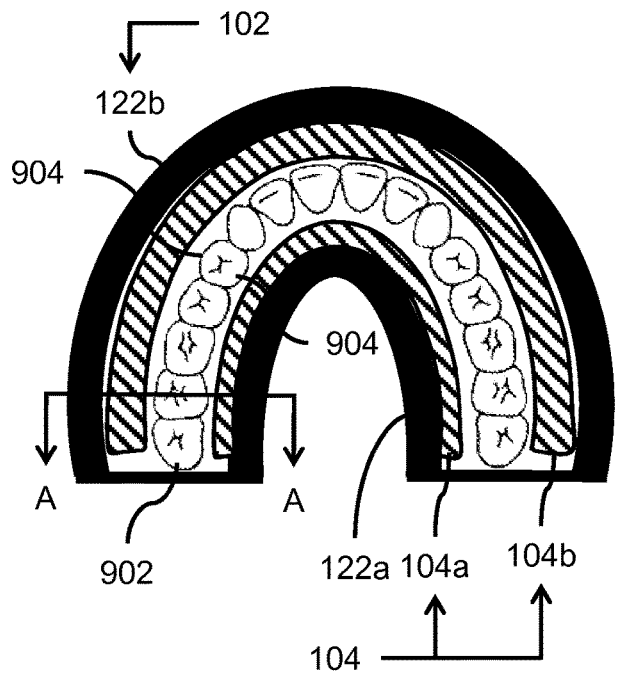
FIGS. 4A to 4I depict views of embodiments of the apparatus of FIG. 1.
Figure 4B:
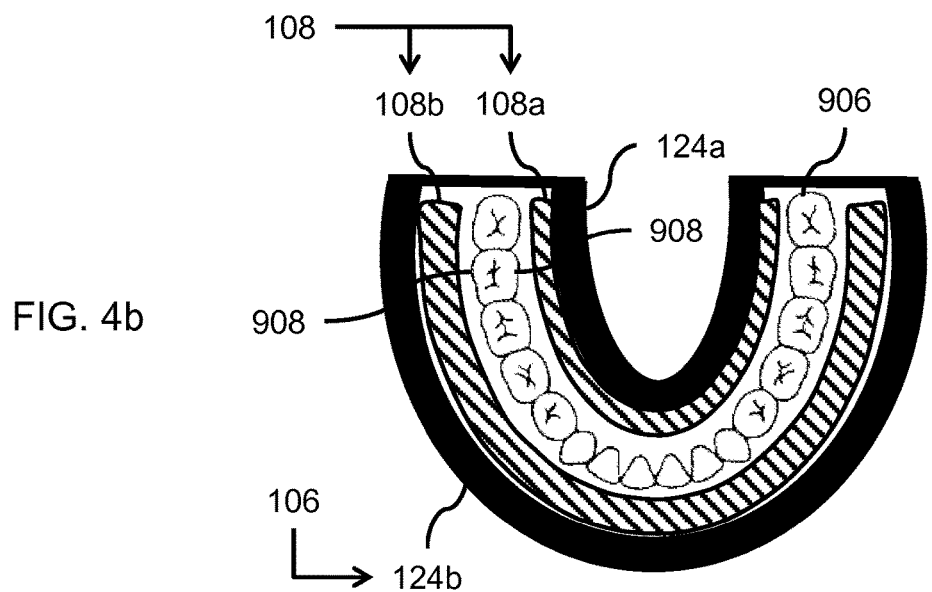
Figure 4C:
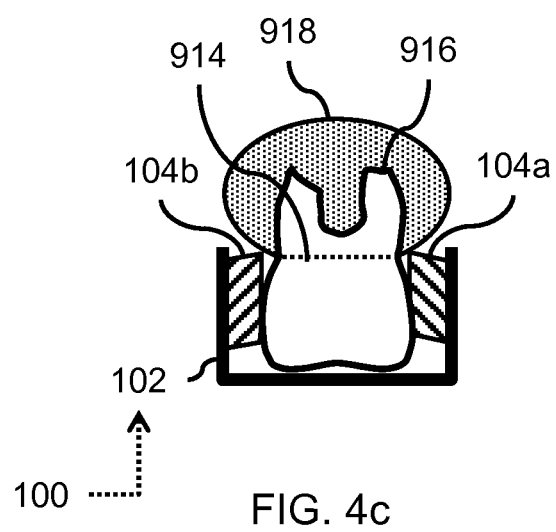
Figure 4D:
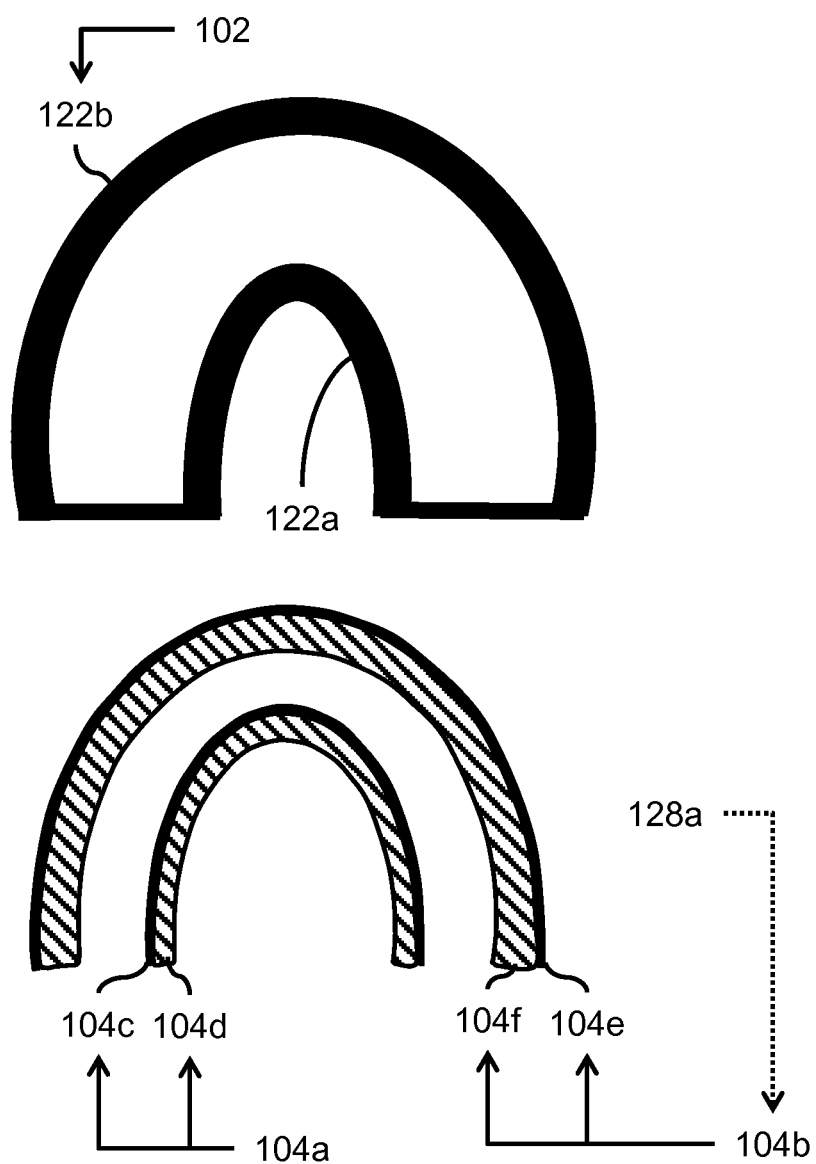
Figure 4E:
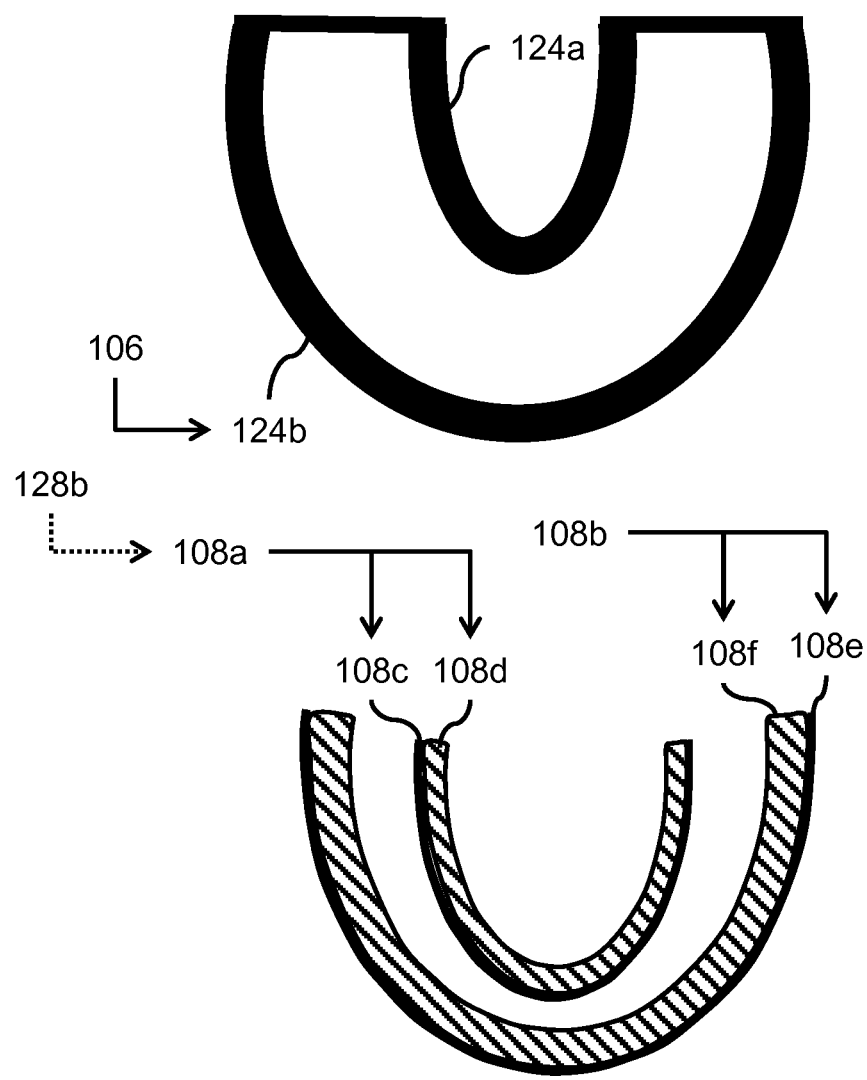
Figure 4F:
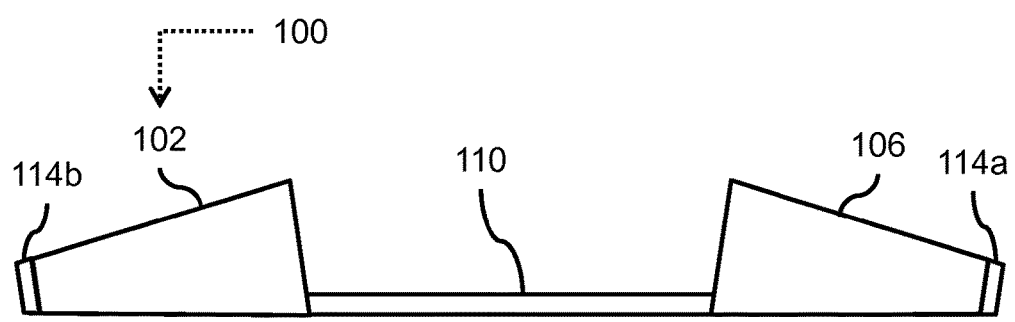
Figure 4G:
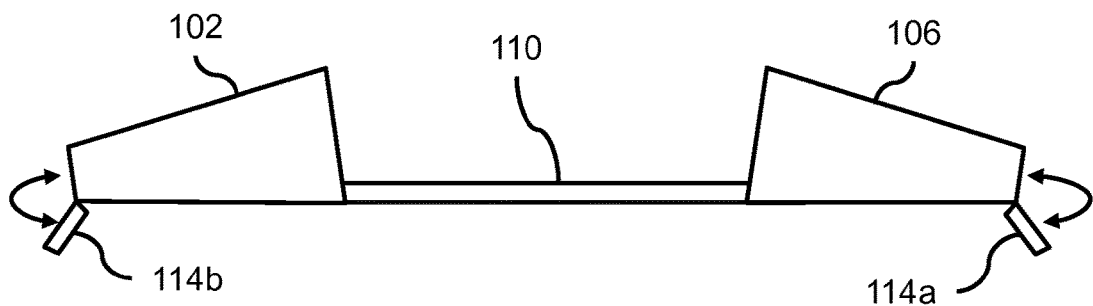

FIGS. 4A to 4I depict views of embodiments of the apparatus 100 for the user 900 (depicted in FIG. 3) having a mouth 901 leading to an oral cavity in which upper teeth 902 having upper opposite sides 904 (depicted in FIG. 4A) are positioned, and in which lower teeth 906 having lower opposite sides 908 (depicted in FIG. 4A) are positioned. FIGS. 4A, 4B, 4D, 4E, 4H, and 4I depict top views. FIG. 4C depicts a cross-sectional view taken along line A-A of FIG. 4A. FIGS. 4F and 4G depict side views.

Referring to the embodiments depicted in FIG. 4A and FIG. 4B, The apparatus 100 is for the user 900 having a mouth 901 leading to an oral cavity in which upper teeth 902 (the crown portion of the teeth are exposed) having upper opposite sides 904 are positioned, and in which lower teeth 906 (the crown portion of the teeth are exposed) having lower opposite sides 908 are positioned.

The apparatus 100 includes the upper oral delivery mouthpiece 102, am upper tooth-bristle assembly 104, the lower oral delivery mouthpiece 106, and a lower tooth-bristle assembly 108.

As previously described, the upper oral delivery mouthpiece 102 is configured to cradle, at least in part, the upper teeth 902 of the user 900 once the upper oral delivery mouthpiece 102 is operatively received in the mouth 901 of the user 900 just so. The upper oral delivery mouthpiece 102 is configured to: (A) face the upper teeth 902 of the user 900, (B) face, at least in part, an upper arch of the mouth 901 of the user 900, and (C) surround, at least in part, upper opposite sides 904 of the upper teeth 902 of the user 900. The upper oral delivery mouthpiece 102 has distal ends positioned proximate to each other.

As previously described, the lower oral delivery mouthpiece 106 is configured to cradle, at least in part, the lower teeth 906 of the user 900 once the lower oral delivery mouthpiece 106 is operatively received in the mouth 901 of the user 900 just so. The lower oral delivery mouthpiece 106 is configured to: (A) face the lower teeth 906 of the user 900, (B) face, at least in part, a lower arch of the mouth 901 of the user 900, and (C) surround, at least in part, lower opposite sides 908 of the lower teeth 906 of the user 900. The lower oral delivery mouthpiece 106 has distal ends positioned proximate to each other.

In general terms, the upper tooth-bristle assembly 104 is configured to operatively affix to the upper oral delivery mouthpiece 102. The is done in such a way that the upper tooth-bristle assembly 104 faces the upper opposite sides 904 of the upper teeth 902 of the user 900 once the upper oral delivery mouthpiece 102 is operatively received in the mouth 901 of the user 900 just so.

More specifically, the upper oral delivery mouthpiece 102 includes an inner wall assembly 122a and an outer wall assembly 122b spaced apart from the inner wall assembly 124a. The upper tooth-bristle assembly 104 includes a first upper tooth-bristle assembly 104a and a second upper tooth-bristle assembly 104b. The first upper tooth-bristle assembly 104a is configured to operatively affix to the inner wall assembly 122a of the upper oral delivery mouthpiece 102. The second upper tooth-bristle assembly 104b is configured to operatively affix to the outer wall assembly 122b of the upper oral delivery mouthpiece 102.

In general terms, the lower tooth-bristle assembly 108 is configured to operatively affix to the lower oral delivery mouthpiece 106. The is done in such a way that the lower tooth-bristle assembly 108 faces the lower opposite sides 908 of the lower teeth 906 of the user 900 once the lower oral delivery mouthpiece 106 is received in the mouth 901 of the user 900.

More specifically, the lower oral delivery mouthpiece 106 includes an inner wall assembly 124a and an outer wall assembly 124b spaced apart from the inner wall assembly 124a. The lower tooth-bristle assembly 108 includes a first lower tooth-bristle assembly 108a and a second lower tooth-bristle assembly 108b. The first lower tooth-bristle assembly 108a is configured to operatively affix to the inner wall assembly 124a of the lower oral delivery mouthpiece 106. The second lower tooth-bristle assembly 108b is configured to operatively affix to the outer wall assembly 124b of the lower oral delivery mouthpiece 106.

Referring to the embodiment depicted in FIG. 4A, the upper tooth-bristle assembly 104 and the lower tooth-bristle assembly 108 each include (in accordance with an option) a flexible bristle material (and any equivalent thereof). The upper tooth-bristle assembly 104 and the lower tooth-bristle assembly 108 each include (in accordance with an option) a microfiber material, such as an extra soft type bristle (and any equivalent thereof).

Referring to the embodiment depicted in FIG. 4A and FIG. 4B, the upper tooth-bristle assembly 104 and the lower tooth-bristle assembly 108 each includes (in accordance with an option) colored bristles configured to allow for contrast. Since teeth are relatively white, the colored bristles help the user to facilitate visual location of the gum line 914 (depicted in FIG. 4C).

Referring to the embodiment depicted in FIG. 4C, the upper tooth-bristle assembly 104 and the lower tooth-bristle assembly 108 are each configured (in accordance with an option) to be directionally aligned, at least in part, from a biting part once the upper oral delivery mouthpiece 102 and the lower oral delivery mouthpiece 106 are operatively received in the mouth 901 of the user 900. For the case where the apparatus 100 (depicted in FIG. 3) is seated into the mouth 901 of the user 900, the biting part is the inner part where the bristles of the upper tooth-bristle assembly 104 and the lower tooth-bristle assembly 108 touch (at least in part) the occlusal and/or biting surface of a tooth. The biting part is aligned along the sidewalls of the upper oral delivery mouthpiece 102 and the lower oral delivery mouthpiece 106 eventually directionally aligned toward the pockets surrounding the tooth of the user 900 once the plastic u-shaped mouthpiece is received in the mouth 901 of the user 900. The upper tooth-bristle assembly 104 is configured to clean the gum line 914 positioned along the tooth 916 extending below or from the gum 918 of the user 900.

Referring to the embodiment depicted in FIG. 4C, the upper tooth-bristle assembly 104 and the lower tooth-bristle assembly 108 are each configured to be directionally aligned, at least in part, upward to about 45 degrees toward the pockets that surround the upper teeth 902 and the lower teeth 906, respectively, of the user 900 once the upper oral delivery mouthpiece 102 and the lower oral delivery mouthpiece 106 are operatively received in the mouth 901 of the user 900. The bristles of the upper tooth-bristle assembly 104 and the lower tooth-bristle assembly 108 are angled gradually moving from the biting part to along the sidewalls of the upper oral delivery mouthpiece 102 and the lower oral delivery mouthpiece 106 eventually moving upwards at a 45-degree angle. In this arrangement, the pockets may be cleaned (the pocket surround a tooth).

Referring to the embodiment depicted in FIG. 4D and FIG. 4E, the upper oral delivery mouthpiece 102 and the upper tooth-bristle assembly 104 are configured to be (in accordance with an option): (A) selectively attachable to each other; and (B) selectively detachable from each other.

In accordance with the embodiment depicted in FIGS. 4D and 4E, the upper oral delivery mouthpiece 102 is configured to operatively receive an upper attachment assembly 128a such as, an upper replaceable insert, the first upper tooth-bristle assembly 104a and/or the second upper tooth-bristle assembly 104b. The upper attachment assembly 128a is configured to provide, at least in part, oral treatment to the upper teeth 902 of the user 900. The lower oral delivery mouthpiece 106 is configured to operatively receive a lower attachment assembly 128b such as, a lower replaceable insert, the first lower tooth-bristle assembly 108a and/or the second lower tooth-bristle assembly 108b. The lower attachment assembly 128b is configured to provide, at least in part, oral treatment to the lower teeth 906 of the user 900.

In accordance with an embodiment, the upper attachment assembly 128a is selected from a group of inserts consisting of a brushing field, a clear plastic tray, an orthodontic brushing field with angled bristles (for orthodontic patients), a brushing field angled at 45 degrees, a UV treatment insert (for killing bacteria, disinfecting)), a whitening treatment insert (for whitening teeth). The lower attachment assembly 128b is selected from a group of inserts consisting of a brushing field, a clear plastic tray, an orthodontic brushing field with angled bristles (for orthodontic patients), a brushing field angled at 45 degrees, a UV treatment insert (for killing bacteria, disinfecting)), a whitening treatment insert (for whitening teeth). The upper oral delivery mouthpiece 102 and the lower oral delivery mouthpiece 106 may be unitary with the upper attachment assembly 128a and the lower attachment assembly 128b (respectively).

More specifically, the first upper tooth-bristle assembly 104a includes an upper base section 104c and an upper bristle field 104d extending from the upper base section 104c. The upper base section 104c is configured to be selectively attachable to (and selectively detachable from) the inner wall assembly 122a of the upper oral delivery mouthpiece 102. More specifically, the second upper tooth-bristle assembly 104b includes an upper base section 104e and an upper bristle field 104f extending from the upper base section 104e. The upper base section 104e is configured to be selectively attachable to (and selectively detachable from) the outer wall assembly 122b of the upper oral delivery mouthpiece 102. This is done in such a way that once attached, the first upper tooth-bristle assembly 104a and the second upper tooth-bristle assembly 104b are operatively positioned within the upper oral delivery mouthpiece 102.

Referring to the embodiment depicted in FIG. 4E, and more specifically, the first lower tooth-bristle assembly 108a includes a lower base section 108c and a lower bristle field 108d extending from the lower base section 108c. The lower base section 108c is configured to be selectively attachable to (and selectively detachable from) the inner wall assembly 124a of the lower oral delivery mouthpiece 106. More specifically, the second lower tooth-bristle assembly 108b includes a lower base section 108e and a lower bristle field 108f extending from the lower base section 108e. The lower base section 108e is configured to be selectively attachable to (and selectively detachable from) the outer wall assembly 124b of the lower oral delivery mouthpiece 106. This is done in such a way that once attached, the first lower tooth-bristle assembly 108a and the second lower tooth-bristle assembly 108b are operatively positioned within the lower oral delivery mouthpiece 106.

Referring to the embodiment depicted in FIG. 4E, the lower oral delivery mouthpiece 106 and the lower tooth-bristle assembly 108 are configured to be (in accordance with an option) (A) selectively attachable to each other, and (B) selectively detachable from each other.

Referring to the embodiments depicted in FIG. 4D and FIG. 4E, the upper tooth-bristle assembly 104 and the lower tooth-bristle assembly 108 are configured to be (in accordance with an option) any one of used individually (separately) and used together in the mouth 901 of the user 900. For instance, the user 900 may use the apparatus 100 to just clean the upper teeth 902 or just clean the lower teeth 906. For instance, this may be done by positioning the upper oral delivery mouthpiece 102 outside of the mouth 901 of the user 900, and positioning the lower oral delivery mouthpiece 106 in the mouth 901 of the user 900 (the user 900 can still grasp the handle assembly 110 and clean the lower teeth 906 without cleaning the upper teeth 902). This arrangement may be useful for a user that suffers with a gag reflux or is edentulous in one arch (or any other reason), then the user has the option (advantageously) to clean and/or treat either the upper teeth 902 or lower teeth 906 (one at a time, one after the other).

Referring to the embodiments depicted in FIG. 4D and FIG. 4E, the upper oral delivery mouthpiece 102 and the upper tooth-bristle assembly 104 are configured to be (in accordance with an option): (A) selectively attachable to each other; and (B) selectively detachable from each other. The lower oral delivery mouthpiece 106 and the lower tooth-bristle assembly 108 are configured to be (A) selectively attachable to each other, and (B) selectively detachable from each other. Once the upper tooth-bristle assembly 104 is removed from the upper oral delivery mouthpiece 102 and the lower tooth-bristle assembly 108 is removed from the lower oral delivery mouthpiece 106, the upper oral delivery mouthpiece 102 and the lower oral delivery mouthpiece 106 are usable an agent delivery system. The agent delivery system is configured to deliver a bleaching compound or a therapeutic agent to the teeth (once the apparatus 100 is received in the mouth 901 of the user 900). This option allows for the upper tooth-bristle assembly 104 and the lower tooth-bristle assembly 108 to be removed and replaced (taken out from the apparatus 100). This is done in such a way that the u-shaped mouthpieces can be used as a delivery system and/or to deliver a bleaching compound or a therapeutic agent to the teeth (once the upper oral delivery mouthpiece 102 and lower oral delivery mouthpiece 106 are received in the mouth 901 of the user 900). The upper tooth-bristle assembly 104 and the lower tooth-bristle assembly 108 are configured to be selectively connected to the upper oral delivery mouthpiece 102 and the lower oral delivery mouthpiece 106 (respectively). This option allows for the upper tooth-bristle assembly 104 and the lower tooth-bristle assembly 108 to be replaced, so the mouth 901 piece housing may be used as an agent deliver system (if desired) to deliver whitening, bleaching, and/or a therapeutic component to the teeth. The upper tooth-bristle assembly 104 and the lower tooth-bristle assembly 108 are generally horseshoe shaped devices configured to clean the opposite sides of the teeth. The upper tooth-bristle assembly 104 and the lower tooth-bristle assembly 108 surround (at least in part) the teeth.

For instance, the upper tooth-bristle assembly 104 and the lower tooth-bristle assembly 108 are configured to be snap fitted to the upper oral delivery mouthpiece 102 and the lower oral delivery mouthpiece 106 (if so desired), and any other well-known structural elements may be used to selectively attach and detach the upper tooth-bristle assembly 104 and the lower tooth-bristle assembly 108 to the upper oral delivery mouthpiece 102 and the lower oral delivery mouthpiece 106 (respectively). For instance, a button structure (well known and not further described in detail) may be used to selective connect the upper tooth-bristle assembly 104 and the lower tooth-bristle assembly 108 to the upper oral delivery mouthpiece 102 and the lower oral delivery mouthpiece 106. This technical feature may be configured to facilitate placement of different angled bristles (such as, bristles angled for patients who are in orthodontic treatment). For instance, having or arranging the bristles angled upward from the bite part and bristles angled downward in such a way that the bristles coming together (at least in part) to form a v-shaped structure. In this manner, the bristles may clean the top and bottoms effectively of orthodontic brackets placed in the mouth 901 of the user 900.

Figure 4H:
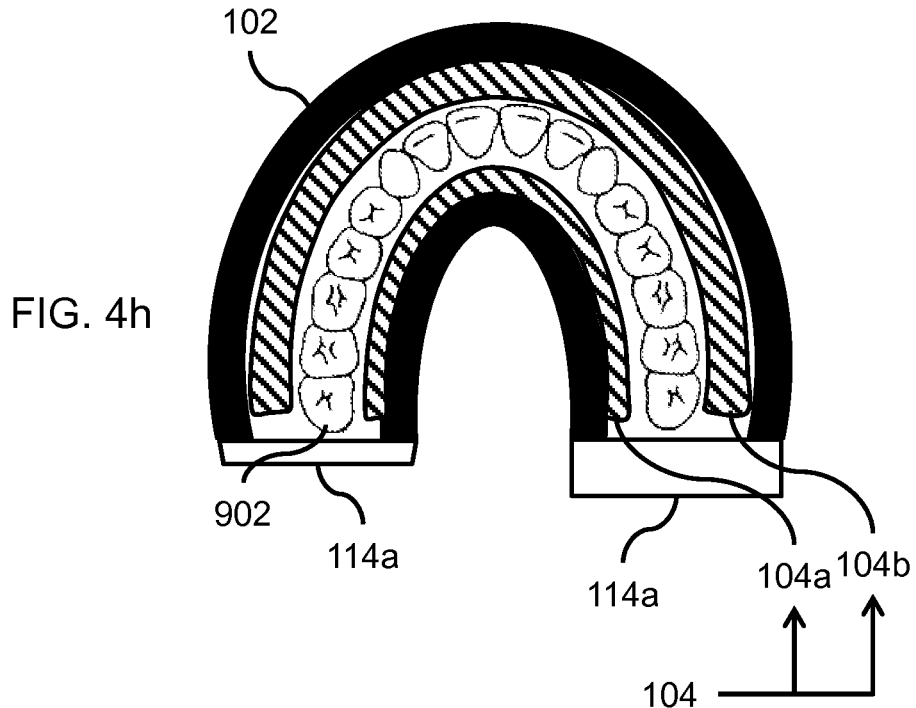
Figure 4I:
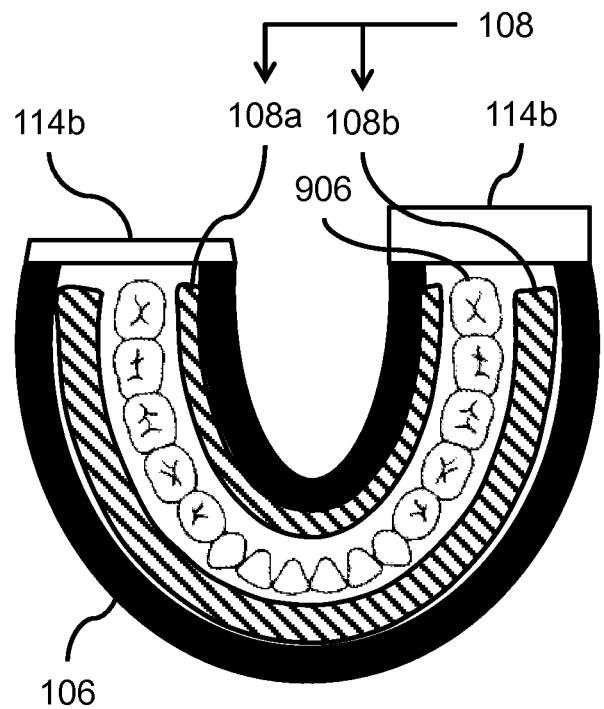

Referring to the embodiments depicted in FIGS. 4F, 4G, 4H and 4I, the apparatus 100 further includes a first movable flap assembly 114a positioned at each distal end of the upper oral delivery mouthpiece 102. The first movable flap assembly 114a is configured to adjustably contact the molars of the user 900 once the upper oral delivery mouthpiece 102 is received in the mouth 901 of the user 900 (to adjust to the different last molar anatomy and arch sizes). The apparatus 100 also includes a second movable flap assembly 114b positioned at each distal end of the lower oral delivery mouthpiece 106. The second movable flap assembly 114b is configured to adjustably contact the molars of the user 900 once the lower oral delivery mouthpiece 106 is received in the mouth 901 of the user 900 (to adjust to the different last molar anatomy and arch sizes). FIGS. 4F and 4G depict side views of the apparatus 100. FIGS. 4H and 4I depict top views of the apparatus 100. The first movable flap assembly 114a is pivotally attached to the upper oral delivery mouthpiece 102. The second movable flap assembly 114b is pivotally attached to the lower oral delivery mouthpiece 106.

Referring to FIG. 4H, the instance of the first movable flap assembly 114a positioned on the right side of the page is placed in the open position (corresponding to the position depicted in FIG. 4G). Referring to FIG. 4H, the instance of the first movable flap assembly 114a positioned on the left side of the page is placed in the closed position (corresponding to the position depicted in FIG. 4F).

Referring to FIG. 4H, the instance of the second movable flap assembly 114b positioned on the right side of the page is placed in the open position (corresponding to the position depicted in FIG. 4G). Referring to FIG. 4H, the instance of the second movable flap assembly 114b positioned on the left side of the page is placed in the closed position (corresponding to the position depicted in FIG. 4F).

The first movable flap assembly 114a and the second movable flap assembly 114b mitigate, at least in part, problems associated with cleaning crowded teeth and/or to wraps around (at least in part) the last molar. This arrangement allows for a more thorough cleaning of the molars that are partially erupted and or molars that sit very close to the gum line 914 (depicted in FIG. 4C). The first movable flap assembly 114a and the second movable flap assembly 114b are configured to allow to adjust to those areas that are prone to cavities.

Figure 5:
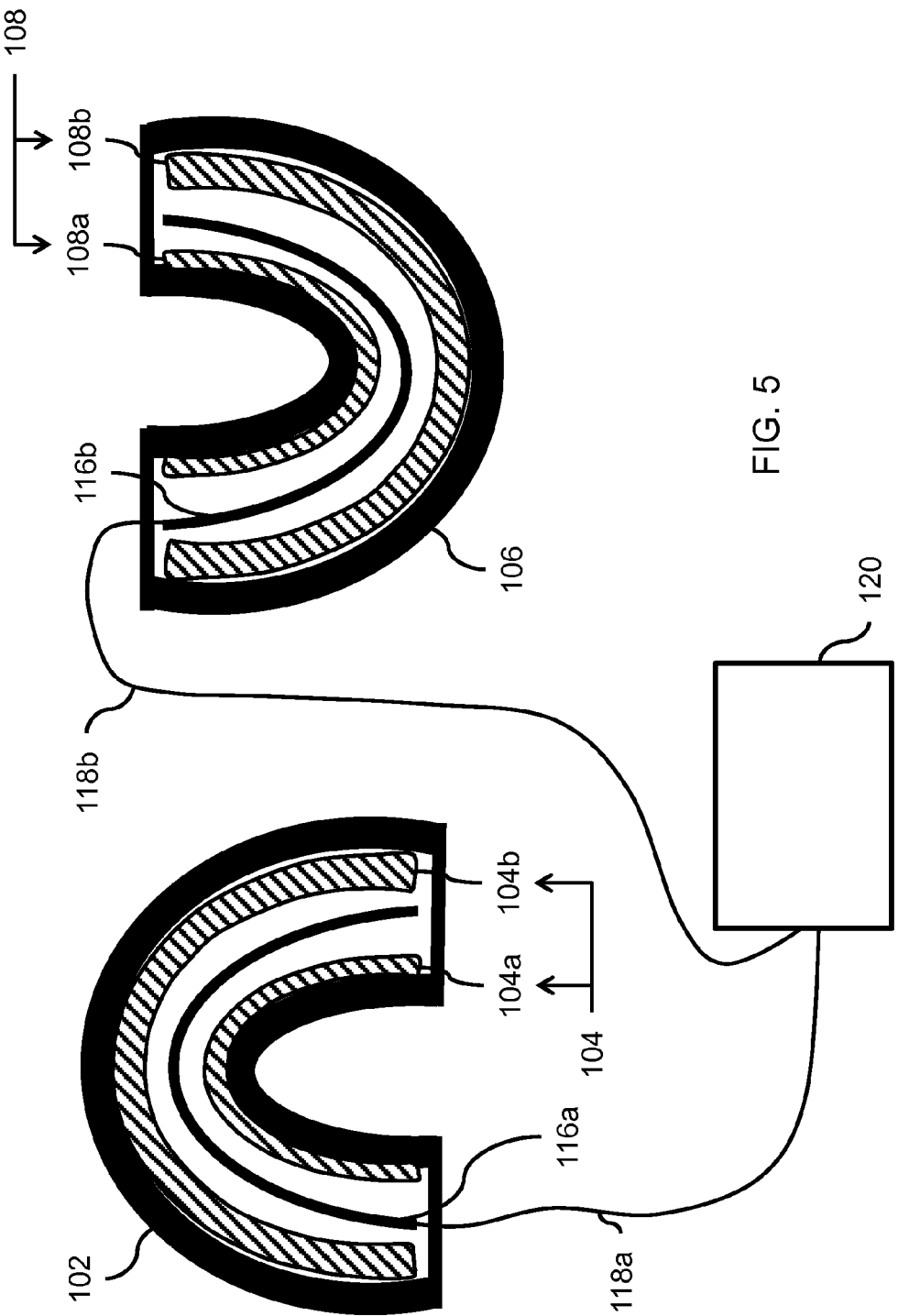
FIG. 5 depicts a view of an embodiment of the apparatus of FIG. 1.

FIG. 5 depicts a view of an embodiment of the apparatus 100 for the user 900 (depicted in FIG. 3) having a mouth 901 leading to an oral cavity in which upper teeth 902 having upper opposite sides 904 (depicted in FIG. 4A) are positioned, and in which lower teeth 906 having lower opposite sides 908 (depicted in FIG. 4A) are positioned. FIG. 5 depicts a top view.

Referring to the embodiment depicted in FIG. 5, the apparatus 100 further includes an upper optical fiber 116a, a lower optical fiber 116b, and an light-treatment assembly 120. For instance, the light-treatment assembly 120 is configured to emit an ultra violet light and/or a teeth-whitening light. The upper optical fiber 116a is configured to be operatively received in the upper oral delivery mouthpiece 102. The lower optical fiber 116b is configured to be operatively received in the lower oral delivery mouthpiece 106. The light-treatment assembly 120 is configured to operatively interface with the upper optical fiber 116a and the lower optical fiber 116b. The light-treatment assembly 120 is configured to provide ultra violet light to the upper optical fiber 116a and the lower optical fiber 116b. This is done in such a way that any bacteria positioned in the upper oral delivery mouthpiece 102 and the lower oral delivery mouthpiece 106 is killed, at least in part, once the upper optical fiber 116a and the lower optical fiber 116b are positioned in the upper oral delivery mouthpiece 102 and the lower oral delivery mouthpiece 106, respectively. The light-treatment assembly 120 may be configured to function to provide a tooth whitening light (if so desired, also called a tooth-whitening agent). The upper optical fiber 116a and the lower optical fiber 116b may be configured to be clipped (attachable) to the upper oral delivery mouthpiece 102 and the lower oral delivery mouthpiece 106 (respectively). The upper optical fiber 116a and the lower optical fiber 116b are configured to emit UV (ultra-violet) light from the front, the sides, and along the body of the upper oral delivery mouthpiece 102 and/or the lower oral delivery mouthpiece 106.

In accordance with an option, a first wire 118a (fiber optic cable) is configured to connect the upper optical fiber 116a to the light-treatment assembly 120. A second wire 118b is configured to connect the lower optical fiber 116b to the light-treatment assembly 120.

In accordance with an embodiment, the upper attachment assembly 128a and the lower attachment assembly 128b are selected from a group of inserts consisting of a brushing field, a clear plastic tray, an orthodontic brushing field with angled bristles, a brushing field angled at about 45 degrees, an ultra violet light treatment insert, and a whitening treatment insert.

Figure 6A:
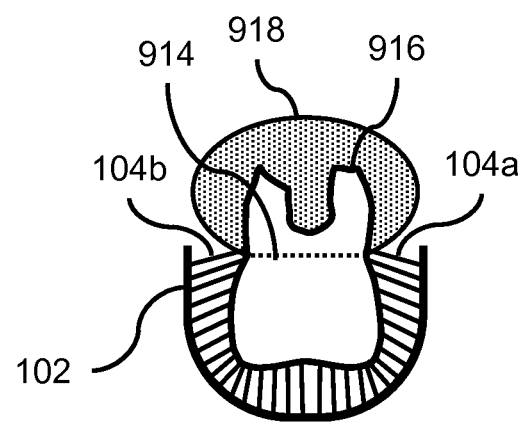
FIGS. 6A and 6B depicts a view of an embodiments of the apparatus of FIG. 1.
Figure 6B:
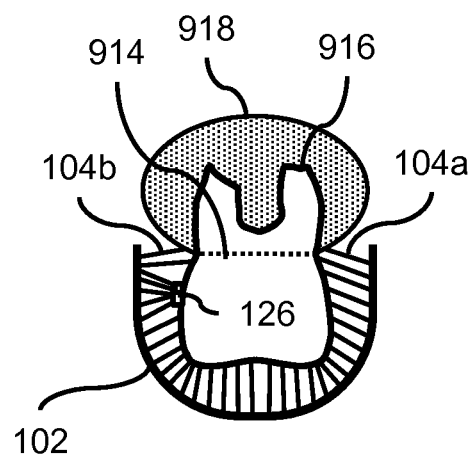

FIGS. 6A and 6B depict views of an embodiment of the apparatus of FIG. 1. FIGS. 6A and 6B depict cross sectional views taken along line A-A of FIG. 4A.

FIG. 6A depicts an embodiment in which the upper oral delivery mouthpiece 102 includes the second upper tooth-bristle assembly 104b. The second upper tooth-bristle assembly 104b includes a bristle pattern configured to extend at about 45 degrees upwardly toward the gum line 914 of the tooth 916. In this manner, the portion of the tooth 916 positioned next to the gum line 914 may be cleaned somewhat better. It will be appreciated that the same configuration may be implemented on the first upper tooth-bristle assembly 104a (if so desired).

FIG. 6B depicts an embodiment in which an ortho bracket 126 is operatively mounted to the side wall of the tooth 916. For this embodiment, the second upper tooth-bristle assembly 104b includes a v-shaped bristle pattern positioned adjacent to or proximate to the ortho bracket 126. The apex of the v-shaped bristle pattern is pointed generally toward the ortho bracket 126. In this manner, portions of the tooth 916 located around the ortho bracket 126 may be more properly cleaned with the v-shaped bristle pattern (once the upper oral delivery mouthpiece 102 is moved relative to the tooth 916). In addition, the second upper tooth-bristle assembly 104b also includes a bristle pattern configured to extend at about 45 degrees upwardly toward the gum line 914 of the tooth 916. It will be appreciated that the same configuration may be implemented on the first upper tooth-bristle assembly 104a (if so desired).

This written description uses examples to disclose the invention, including the best mode, and also to enable any person skilled in the art to make and use the invention. The patentable scope of the invention is defined by the claims, and may include other examples that occur to those skilled in the art. Such other examples are within the scope of the claims if they have structural elements that do not differ from the literal language of the claims, or if they include equivalent structural elements with insubstantial differences from the literal language of the claims.

It may be appreciated that the assemblies and modules described above may be connected with each other as required to perform desired functions and tasks within the scope of persons of skill in the art to make such combinations and permutations without having to describe each and every one in explicit terms. There is no particular assembly, or component that may be superior to any of the equivalents available to the person skilled in art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

What is claimed is:

1. An apparatus for a user having a mouth leading to an oral cavity in which upper teeth having upper opposite sides are positioned, and in which lower teeth having lower opposite sides are positioned, the apparatus comprising:

an upper oral delivery mouthpiece being configured to be positioned in the mouth of the user in such a way that the upper oral delivery mouthpiece provides, at least in part, oral treatment to the upper teeth of the user once the upper oral delivery mouthpiece is operatively received in the mouth of the user just so; and a lower oral delivery mouthpiece being configured to be positioned in the mouth of the user in such a way that the lower oral delivery mouthpiece provides, at least in part, oral treatment to the lower teeth of the user once the lower oral delivery mouthpiece is operatively received in the mouth of the user just so; and the upper oral delivery mouthpiece includes:

an upper bendable assembly being embedded in the upper oral delivery mouthpiece, and the upper bendable assembly being configured to urge the upper oral delivery mouthpiece to conform, at least in part, to a curvature of the upper teeth of the user; and the lower oral delivery mouthpiece includes:

a lower bendable assembly being embedded in the lower oral delivery mouthpiece, and the lower bendable assembly being configured to urge the lower oral delivery mouthpiece to conform, at least in part, to a curvature of the lower teeth of the user; and wherein:

the upper oral delivery mouthpiece and the lower oral delivery mouthpiece are each also configured to face the side of the teeth that is located adjacent to the inside of the cheeks of the user once the upper oral delivery mouthpiece and the lower oral delivery mouthpiece are received in the mouth of the user; and the upper oral delivery mouthpiece and the lower oral delivery mouthpiece are each also configured to face the side of the teeth that is located adjacent to the tongue of the user once the upper oral delivery mouthpiece and the lower oral delivery mouthpiece are operatively received in the mouth of the user; and the upper bendable assembly and the lower bendable assembly are each also configured to be bendable in such a way that the upper bendable assembly and the lower bendable assembly, in use, conform to the curvature of the upper teeth of the user separately from the curvature of the lower teeth of the user; and the upper oral delivery mouthpiece is configured to include an upper tooth-bristle assembly, in which the upper tooth-bristle assembly, in use, faces the upper teeth of the user once the upper oral delivery mouthpiece is operatively received in the mouth of the user in such a way that the upper tooth-bristle assembly, in use, faces (A) the side of the teeth that is located adjacent to the inside of the cheeks of the user, and (B) the side of the teeth that is located adjacent to the tongue of the user; and the lower oral delivery mouthpiece is configured to include a lower tooth-bristle assembly, in which the lower tooth-bristle assembly, in use, faces the lower teeth of the user once the lower oral delivery mouthpiece is operatively received in the mouth of the user in such a way that the lower tooth-bristle assembly, in use, faces (A) the side of the teeth that is located adjacent to the inside of the cheeks of the user, and (B) the side of the teeth that is located adjacent to the tongue of the user; and the upper oral delivery mouthpiece is also configured to position the upper tooth-bristle assembly proximate to the teeth of the user once the upper oral delivery mouthpiece is operatively received in the mouth of the user, and the lower oral delivery mouthpiece is configured to also position the lower tooth-bristle assembly proximate to the teeth of the user once the upper oral delivery mouthpiece is operatively received in the mouth of the user, in such a way that the upper tooth-bristle assembly and the lower tooth-bristle assembly, in use, contact a range of teeth widths of the teeth of the user; and the upper bendable assembly and the lower bendable assembly are each also configured to be manipulated in such a way that the upper bendable assembly and the lower bendable assembly, in use, are formed to fit the upper oral delivery mouthpiece and the lower oral delivery mouthpiece to the unique curves of the dental arches of the upper teeth and the lower teeth including crowded teeth, misshaped teeth, misaligned teeth or misshaped dental arches; and the upper bendable assembly and the lower bendable assembly are each also configured to be manipulated in such a way that the upper bendable assembly and the lower bendable assembly, in use, remain formed to fit to the unique curves of the dental arches of the upper teeth and the lower teeth of the user once the upper oral delivery mouthpiece and the lower oral delivery mouthpiece are removed from the mouth of the user having crowded teeth, misshaped teeth, misaligned teeth or misshaped dental arches.

2. The apparatus of claim 1, wherein the upper oral delivery mouthpiece is configured to operatively receive an upper attachment assembly being configured to provide, at least in part, oral treatment to the upper teeth of the user, and the lower oral delivery mouthpiece is configured to operatively receive a lower attachment assembly being configured to provide, at least in part, oral treatment to the lower teeth of the user.

3. The apparatus of claim 2, wherein the upper attachment assembly and the lower attachment assembly are selected from a group of inserts consisting of a brushing field, a clear plastic tray, an orthodontic brushing field with angled bristles, a brushing field angled at about 45 degrees, an ultra violet light treatment insert, and a whitening treatment insert.

4. The apparatus of claim 1, further comprising:
a first movable flap assembly being positioned at each distal end of the upper oral delivery mouthpiece, and the first movable flap assembly being configured to adjustably contact the molars of the user once the upper oral delivery mouthpiece is received in the mouth of the user just so; and
a second movable flap assembly being positioned at each distal end of the lower oral delivery mouthpiece, and the second movable flap assembly being configured to adjustably contact the molars of the user once the lower oral delivery mouthpiece is received in the mouth of the user just so.

5. The apparatus of claim 1, further comprising:
a handle assembly being configured to operatively attach to the upper oral delivery mouthpiece, and to attach to the lower oral delivery mouthpiece in such a way that the handle assembly is usable for inserting and positioning the upper oral delivery mouthpiece and the lower oral delivery mouthpiece into the mouth of the user.

6. The apparatus of claim 1, wherein the upper oral delivery mouthpiece and the lower oral delivery mouthpiece are configured to be manually operatively movable within the mouth of the user without assistance from an electric power source.

7. The apparatus of claim 5, wherein the handle assembly is configured to:
be resiliently bent to form a u-shape in response to receiving an application of a bending force; and
relax and become resiliently elongated in response to removal of the bending force from the handle assembly.

8. The apparatus of claim 5, wherein the handle assembly is configured to allow relative movement between the upper oral delivery mouthpiece and the lower oral delivery mouthpiece.

9. The apparatus of claim 5, wherein the handle assembly includes:
a first handle assembly being configured to operatively attach to the upper oral delivery mouthpiece; and
a second handle assembly being configured to operatively attach to the lower oral delivery mouthpiece.

10. The apparatus of claim 1, wherein the upper tooth-bristle assembly and the lower tooth-bristle assembly each include one of a microfiber material and a flexible bristle material.

11. The apparatus of claim 1, wherein:
the upper bendable assembly is positioned along the interior of the upper oral delivery mouthpiece, and the upper bendable assembly is configured to:
bend in response to receiving a predetermined amount of a bending force in such a way that the upper oral delivery mouthpiece, in use bends and conforms, at least in part, to the curvature of the upper teeth of the user for improved adaptation to the upper teeth of the user, such as to crowded teeth or misshaped teeth; and
not bend in response to not receiving the predetermined amount of the bending force in such a way that the upper oral delivery mouthpiece remains, at least in part, in conforming shape to the curvature of the upper teeth of the user;
the lower bendable assembly is positioned along the interior of the lower oral delivery mouthpiece, and the lower bendable assembly is configured to:
bend in response to receiving the predetermined amount of the bending force in such a way that the lower oral delivery mouthpiece bends and conforms, at least in part, to the curvature of the lower teeth of the user for improved adaptation to the lower teeth of the user, such as to crowded teeth or misshaped teeth; and
not bend in response to not receiving the predetermined amount of the bending force in such a way that the lower oral delivery mouthpiece remains, at least in part, in conforming shape to the curvature of the lower teeth of the user.

12. The apparatus of claim 1, wherein the upper tooth-bristle assembly and the lower tooth-bristle assembly are each configured to be aligned, at least in part, from a biting part once the upper oral delivery mouthpiece and the lower oral delivery mouthpiece are operatively received in the mouth of the user just so.

13. The apparatus of claim 1, wherein the upper tooth-bristle assembly and the lower tooth-bristle assembly are each configured to be directionally aligned, at least in part, upward toward pockets that surround the upper teeth and the lower teeth, respectively, of the user once the upper oral delivery mouthpiece and the lower oral delivery mouthpiece are operatively received in the mouth of the user just so.

14. The apparatus of claim 1, wherein the upper tooth-bristle assembly and the lower tooth-bristle assembly are configured to be any one of used individually separately and used together in the mouth of the user.

15. The apparatus of claim 1, wherein the upper oral delivery mouthpiece and the lower oral delivery mouthpiece each include a flexible silicone material.

16. The apparatus of claim 1, wherein the upper oral delivery mouthpiece and the lower oral delivery mouthpiece each include a flexible plastic material.

17. The apparatus of claim 1, wherein the upper tooth-bristle assembly and the lower tooth-bristle assembly each includes colored bristles configured to allow for contrast.

18. The apparatus of claim 1, wherein:
the upper oral delivery mouthpiece and the upper tooth-bristle assembly are configured to be:
  selectively attachable to each other; and
  selectively detachable from each other; and
the lower oral delivery mouthpiece and the lower tooth-bristle assembly are configured to be:
  selectively attachable to each other; and
  selectively detachable from each other; and
  once the upper tooth-bristle assembly is removed from the upper oral delivery mouthpiece and the lower tooth-bristle assembly is removed from the lower oral delivery mouthpiece, the upper oral delivery mouthpiece and the lower oral delivery mouthpiece are usable as an agent delivery system.

19. The apparatus of claim 1, further comprising:
an upper optical fiber being configured to be operatively received in the upper oral delivery mouthpiece;
a lower optical fiber being configured to be operatively received in the lower oral delivery mouthpiece; and
a light-treatment assembly being configured to operatively interface with the upper optical fiber and the lower optical fiber;
the light-treatment assembly being configured to provide ultra violet light to the upper optical fiber and the lower optical fiber in such a way that any bacteria positioned in the upper oral delivery mouthpiece and the lower oral delivery mouthpiece is killed, at least in part, once the upper optical fiber and the lower optical fiber are positioned in the upper oral delivery mouthpiece and the lower oral delivery mouthpiece, respectively.

* * * * *